United States Patent
Kennard et al.

(10) Patent No.: US 9,557,306 B2
(45) Date of Patent: Jan. 31, 2017

(54) MAGNETICALLY CONTROLLED GAS DETECTORS

(71) Applicant: Honeywell International Inc., Morristown, NJ (US)

(72) Inventors: Clive Warden Kennard, Calgary (CA); Stephen D. Worthington, Calgary (CA); Brandon Eble, Morristown, NJ (US); Tak G. Saruwatari, Calgary (CA); Sean E. Stinson, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 347 days.

(21) Appl. No.: 14/135,800

(22) Filed: Dec. 20, 2013

(65) Prior Publication Data
US 2015/0177207 A1    Jun. 25, 2015

(51) Int. Cl.
*G01N 33/00* (2006.01)

(52) U.S. Cl.
CPC ........ *G01N 33/0027* (2013.01); *G01N 33/007* (2013.01); *G01N 33/0063* (2013.01)

(58) Field of Classification Search
CPC .............. G01N 33/0063; G01N 33/007; G01N 33/0027
See application file for complete search history.

(56) References Cited

U.S. PATENT DOCUMENTS

| | | | | |
|---|---|---|---|---|
| 3,415,108 A | * | 12/1968 | Hubner | G01N 27/16 73/23.2 |
| 3,995,145 A | * | 11/1976 | Harris, III | G06K 7/088 200/46 |
| 4,476,706 A | * | 10/1984 | Hadden | G01N 33/007 73/1.07 |
| 4,821,586 A | * | 4/1989 | Scordato | B01L 3/0227 422/926 |
| 4,897,884 A | * | 1/1990 | Heller | G01D 18/00 340/870.04 |
| 4,984,295 A | * | 1/1991 | Engstrom | H04M 1/72575 455/186.2 |
| 5,363,690 A | | 11/1994 | Evangelista et al. | |
| 5,530,345 A | * | 6/1996 | Murari | H01L 43/065 257/426 |
| 6,442,639 B1 | | 8/2002 | McElhattan et al. | |

(Continued)

OTHER PUBLICATIONS

General Monitors Model S4000CH Intelligent Sensor for Combustible Gas Detection, Part No. MANS4000CH Instruction Manual Revision H05-13. Jun. 30, 2013. Accessed online at <https://web.archive.org/web/20130630080626/http://s7d9.scene7.com/is/content/minesafetyappliances/S4000CH%20Manual>.*

(Continued)

*Primary Examiner* — Lisa Caputo
*Assistant Examiner* — Punam Roy
(74) *Attorney, Agent, or Firm* — Conley Rose, P.C.; Kristin Jordan Harkins (57) ABSTRACT

Non-contact magnetic, optical or RF control elements can be used to control various operational aspects, or parameters of a gas detector. The detector can be placed in a low current, or sleep, mode wherein the operational life-time is not reduced by the duration of the sleep mode. Instructions can be coupled to the detector magnetically, optically, or via RF to alter set points or other operating parameters. Information as to bump tests can also be coupled to the detector.

20 Claims, 5 Drawing Sheets

Bump test in progress instrument not in alarm

Datalog will record bump event not hazardous gas event

Instrument placed in configuration station

Magnet places instrument into configuration mode

(56) References Cited

U.S. PATENT DOCUMENTS

| | | | | |
|---|---|---|---|---|
| 6,987,459 | B2* | 1/2006 | Tice | G08B 21/16 340/632 |
| 7,106,233 | B2* | 9/2006 | Schroeder | G01R 33/07 324/71.3 |
| 7,132,659 | B2 | 11/2006 | Starta et al. | |
| 7,211,909 | B2* | 5/2007 | Schindler | H02K 35/02 310/17 |
| 7,782,193 | B2* | 8/2010 | Goh | A61B 5/0002 340/539.11 |
| 8,358,105 | B2* | 1/2013 | Barten | G01N 33/0009 320/108 |
| 8,537,020 | B2* | 9/2013 | Thorson | G01N 31/22 250/339.13 |
| 9,063,105 | B2* | 6/2015 | Berndt | G01N 27/16 |
| 9,110,041 | B2* | 8/2015 | Flanders | G01N 33/0006 |
| 9,267,923 | B2* | 2/2016 | Urey | G01N 29/022 |
| 2004/0145485 | A1* | 7/2004 | Tice | G08B 21/16 340/632 |
| 2005/0127297 | A1 | 6/2005 | Starta et al. | |
| 2005/0159152 | A1* | 7/2005 | Tice | H04W 52/0219 455/432.1 |
| 2005/0170520 | A1* | 8/2005 | Schur | G01N 1/2273 436/149 |
| 2007/0163367 | A1* | 7/2007 | Sherman | G01R 33/0206 73/866 |
| 2008/0012702 | A1* | 1/2008 | Feight | G01D 3/08 340/539.22 |
| 2008/0266080 | A1* | 10/2008 | Leung | G08C 17/00 340/539.16 |
| 2009/0018785 | A1* | 1/2009 | Huseth | G01R 31/3648 702/63 |
| 2010/0156647 | A1* | 6/2010 | Thorson | G01N 31/22 340/632 |
| 2010/0177684 | A1* | 7/2010 | Kore | H04W 84/18 370/328 |
| 2011/0048100 | A1* | 3/2011 | McEwen | G01N 33/0006 73/1.06 |
| 2012/0007736 | A1 | 1/2012 | Worthington et al. | |
| 2012/0212347 | A1 | 8/2012 | Boone | |
| 2013/0031953 | A1* | 2/2013 | Flanders | G01N 33/0006 73/23.31 |
| 2015/0070188 | A1* | 3/2015 | Aramburu | A01G 25/167 340/870.02 |
| 2015/0102926 | A1* | 4/2015 | Kamalakannan | G06Q 10/0631 340/539.13 |
| 2016/0099517 | A1* | 4/2016 | Fernandes | H01R 12/79 439/39 |

OTHER PUBLICATIONS

Toxic and Combustible Gas Detection, Model D12, Digital Gas Transmitter, product information booklet, www.analyticaltechnology.com, Copyright ©2011 Analytical Technology, Inc.

Net Safety Monitoring Inc., Infrared Combustible Gas Detector User Manual UT-P+-SIR100, www.net-safety.com, Copyright ©2002 Net Safety Monitoring Inc.

General Monitors Model S4000CH Intelligent Sensor for Combustible Gas Detection, publication DS-S4000CH-C1212e data sheet, www.generalmonitors.com, © 2013 General Monitors.

Partial European search report for corresponding EP application 14196850.3, dated Apr. 20, 2015.

Honeywell, Reference Manual: IQ Express Docking Station for MultiPro, Aug. 27, 2012, pp. 1-27.

URL: http://www.honeywellanalytics.com/-/media/honeywell-analytics/products/multipro/documents/english/multipro-iq-express-reference-manual.pdf?la=en.

Extended European Search Report for EP Application Nol. 14196850.3 dated Aug. 28, 2015, 10 pages.

* cited by examiner

MAGNETICALLY CONTROLLED GAS DETECTORS

FIELD

The application pertains to maintenance and control of portable gas detectors. More particularly, the application pertains to control devices used in combination with such detectors to inactivate, or change operating parameters of those detectors.

BACKGROUND

Maintenance free gas detectors are popular in part because they do not need to be turned off and on, they are permanently activated. There is a need for maintenance free gas detectors to last longer on a single battery, but without creating the requirement to have a user turn the unit off and on when needed.

There are multiple problems with using a manual method (like a button) of turning the detector off and on to extend battery life. Users may forget to activate the gas detector and become at risk because their gas detector will not warn them of a dangerous gas level. Additionally, a manual power control switch would give the user the ability to turn off the detector to prevent it from alarming if they know they will be around gas, placing themselves and their co-workers at risk.

Other methods of turning detectors off and on, such as using the existing docking stations would require decisions to be made at the docking station, which can also result in safety risks, and require operator training. Turning the detector off with a docking station also requires costly equipment and may not be an acceptable commercial solution for certain parts of the market, specifically the contractor workforce.

Additionally, there are many situations in which it is beneficial to be able to transfer instructions or data to a portable gas detector to alter its configuration, behavior or state. Generally, expensive and complex circuits, that must be powered, are used to implement such functions.

In yet another circumstance, portable gas detectors are required to be bump tested regularly in order to ensure proper operation. However, bump testing is not intuitive with today's gas detectors. Some manufacturers only support a proper bump test with an expensive docking station, where a series of button presses is required to invoke the bump test. This requires training and is inherently mistake prone.

A low cost alternative to this is to place detectors into a plastic bag and fill the bag with gas, but this doesn't provide the compliance records that safety auditors look for. Ideally, a bump test should be as simple as possible to execute, and it must provide the proper compliance records for auditing purposes. This is very difficult to implement on a gas detector with a single button, which is why the bump test operation is usually controlled and initiated by the docking station. The problem with an exclusively dock initiated bump station is the added cost, size, electrical requirements and complexity of using traditional docking stations for bump tests.

There is thus a continuing need to improve ease of and varieties of control of portable gas detectors.

DETAILED DESCRIPTION

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In one aspect hereof, an automatic method for power cycling that is based on the presence of a simple control device within a proximity to the detector can be provided to meet the customer requirement of delivering longer battery runtime without creating the safety hazards associated with a manual method of turning the detectors off and on. Advantageously this functionality can be provided in a low cost fashion so as to be accessible by customers driven by price.

When the detector is placed on, near or within the control device, the detector is placed into a lower current draw state, or sleep mode. When removed from proximity of the control device, the detector exits the sleep mode and automatically transitions to its regular operating mode.

When in its sleep mode, the remaining lifetime count down circuitry in the detector is disabled. The total remaining operational life time of the detector is not shortened or compromised by the duration of the sleep mode.

The control device can be of active or passive type, employing (for example) a magnet that actuates a magnetic switch inside the detector. An infra-red communication device can also be used in the control device to communicate to the detector through its existing infra-red communications port. Signals from an RFID tag are another way of controlling the sleep/operational mode of the detector. The control device can be included in an instrument docking station, or a small holster that can be worn or attached to the visor of a vehicle for easy access.

A preferred, cost effective, method of building this control device, and having it meet the needs of a customer base that would value it the most would be to develop a small holster, a hibernation case, with an integral magnet. The magnet actuates a magnetic switch inside the gas detector to put the instrument into a sleep mode.

The holster could attach to a sun visor in a vehicle, or be placed in a glove box, and/or be padded so it can reside in a toolbox, simultaneously protecting the detector. When the instrument is inside the holster, it should be visibly obscured such that it would be obvious to a safety manager that the detector is inside its sleep holster. This will reduce the likelihood of people wearing detectors that are deactivated.

In another aspect, embodiments hereof are intended to provide low cost data transfer to a portable gas detector. Advantageously, a passive data transfer solution that is easy to manufacture, easy to use, doesn't require power and is intrinsically safe is provided. Some examples of configuration, behavior or state alterations include changing alarm set points, changing bump test frequency, turning the device on or off, or altering sleep/operating modes of the detector.

Non-contacting magnets can be used to meet the need of a low cost, low power, easy to use and safe way to configure the detector. Data can be transferred to the instrument via a magnetic sensor in the instrument. When the detector interfaces with a passive magnet array, it reads and deciphers control data. This data instructs the detector to implement any of a number of configuration changes, including but not limited to, entering a low power mode or state, exiting low power mode or state, changing alarm set points, or, preparing for bump test.

The information is contained in the orientation of the magnet(s) in a cradle or in a linear array relative to the detector. Unlike the present embodiments, prior art for configuring gas detectors has typically used either infrared or some other computer controlled method of communicating with the detector, or has used the buttons on the detector to manually reconfigure or change detector settings.

In another embodiment, an angular magnetic sensor can be used to detect the angular position of a magnetic field relative to the sensor. This sensor would be located in the portable gas detector. An outside magnet or array of magnets can then be used to create a message. The orientation of each magnet represents the data packet. For example, If the magnetic encoder can decipher the orientation of the magnetic field accurate to one degree, then each magnet can encode 360 possible values, which equates to just over eight bits of information per magnet.

If a singular magnet is used and the orientation of the magnet is controlled in the installation of the cradle the device can easily decipher a single control byte. For a simple device like a single gas instrument, this may provide enough information to control a few simple parameters.

In yet, another embodiment, a linear array of magnets is provided, and the detector is "swiped" past the array. The data held by the angular orientation of the magnets within the array is transferred to the detector. This enables a very low cost passive data transfer solution, which is useful for transferring small packages of data like the configuration of alarm set points for a detector, the bump test frequency, or other policy settings associated with a certain location. These configurations can be customized per customer request.

A third implementation involves using a simple reed switch, and a series of magnets oriented in a straightforward North or South arrangement. As the detector is swiped past the magnets, a simple timing based code can be read, similar to the self-timing nature of bar codes.

In a further aspect hereof, a simple non-powered method is provided for communicating to a gas detector that it is being bump tested by an authorized source. Once the gas detector receives this notification, the gas detector can log information indicating that it is being bump tested. This bump test record, that is stored in the instrument, will provide the necessary compliance information in case of an audit.

With this embodiment, when the user places the gas detector to be bumped close to the bump testing station, the detector receives passively encoded information from the smart bump system, at which time the detector determines that it is being bumped. The detector then records this bump test information in its internal log files. There are no other buttons to press on the detector or bump testing station. The bump test is initiated simply by being in the presence of the authorized bump testing station. In addition, the gas type can be encoded in the passive coding system so that the gas detector will know the type of gas with which it is being bump tested. If for example, the detector is fitted with an H2S sensor and a user attempts to bump test it with a station configured for SO2, this detector will know that the user is trying to bump test with the incorrect gas and the detector can warn the user.

One way of implementing a smart bump system is by using a magnetic coding system, whereby a reader is implemented in the gas detector capable of deciphering the orientation of a magnetic field. The magnetic field is implemented on the bump testing station by implementing a series of, or a single magnet with the desired magnetic orientation.

When the detector is brought into proximity of the magnetic field, the reader in the instrument deciphers the magnetic field orientation and the information is encoded in this orientation. In the case of a reader that is capable of deciphering the angle of a magnetic field accurate to one degree, it is possible to encode 360 states with a single magnet on the bump station. These states could represent different gasses, or in some cases, certain states could be reserved for future use. The implementation may also make use of a combination of a magnetic solution with an RFID or other passive solution. The magnetic field on the bump station could be used to trigger a switch in the gas detector, which then actuates an encoding system capable of sending more data, via RFID. The gas detector could use an internal, powered, RFID reader to read a passive RFID tag located at or, on, the bump station.

Figure 1A:
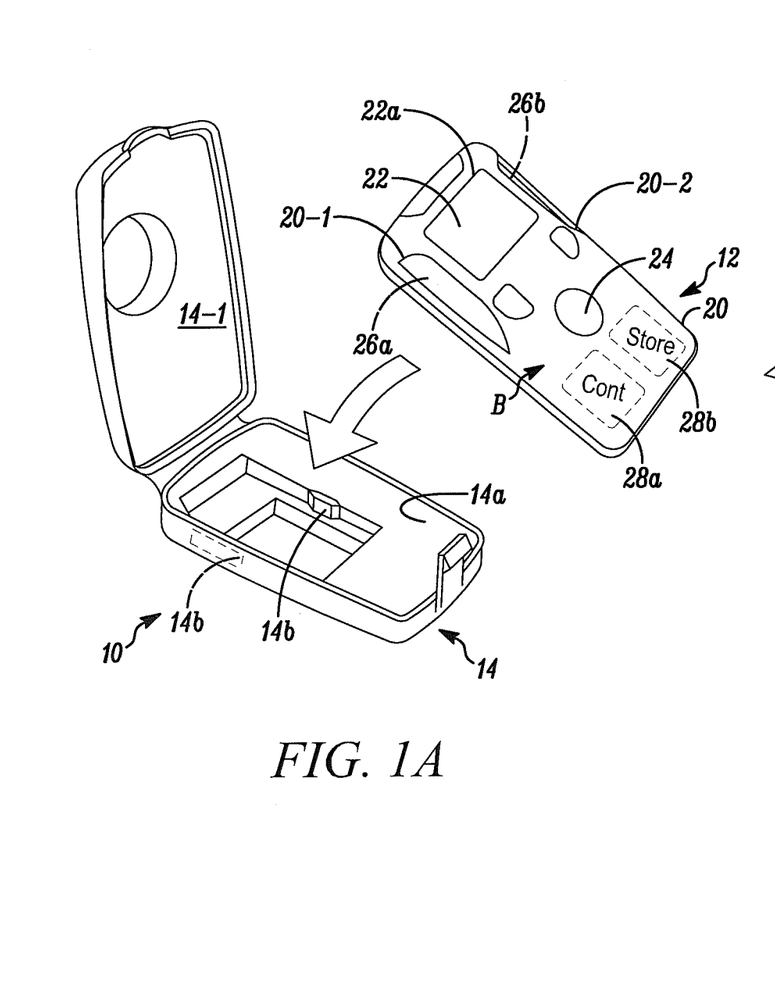
FIG. 1A, 1B together illustrate aspects of a system in accordance herewith.
Figure 1B:
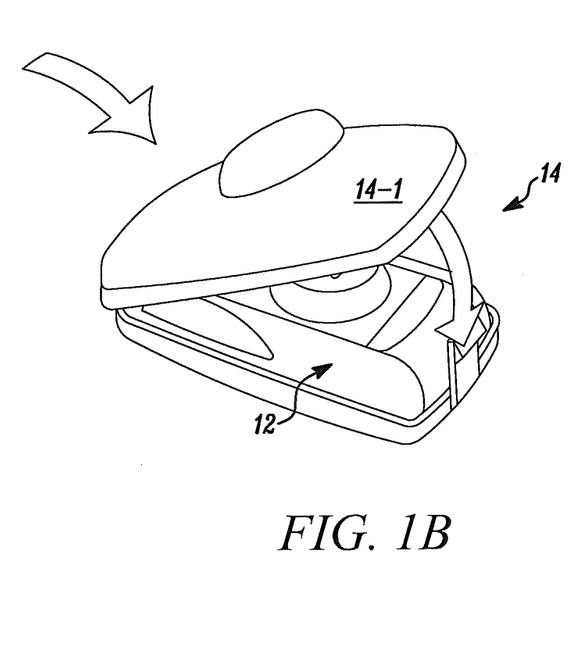

FIGS. 1A, 1B illustrate a system 10 in accordance herewith. The system 10, as illustrated includes a wireless portable detector 12 and an associated hibernation case 14.

Detector 12 includes an external housing 20, with an optical display 22, an audible output device, 22a, a gas sensor and associated gas access ports 24. Housing 20 can also include audible output ports 20-1, -2.

The gas detector 12 can also include one or more non-gas sensors, such as magnetic (reed switch(s) for example), optical or RF sensors 26a, 26b for control purposes. Control circuits 28a, along with a programmable processor and control software, can be coupled the display device 22, gas sensor 24, magnetic, optical or RF sensors 26a, b. Detector 12 can also include a remaining lifetime indicating storage unit 28b.

Case 14 includes a closable cover 14-1 and defines an internal volume 14a which can receive the detector 12. The cover 14-1 is closable with the detector 12 in the region 14a. One or more actuators 14b which could be magnetic, optical or RF are carried by the case 14.

With respect to FIGS. 2A-2E, when the detector 12 is inserted into the case 14, illustrated as FIG. 1A the actuator 14b interacts with at least one sensor, such as 26a of detector 12 and places the detector 12 into a low power draw sleep mode illustrated as in FIG. 1B. The closed cover 14-1 provides optical confirmation that the detector 12 is not active. The sleep mode reduces power drawn from the battery B of detector 12 thereby extending its usable life. Additionally, the remaining lifetime indictor stored in 28b is not reduced while in the sleep mode thereby extending the operational life of detector 12.

Figure 2A:
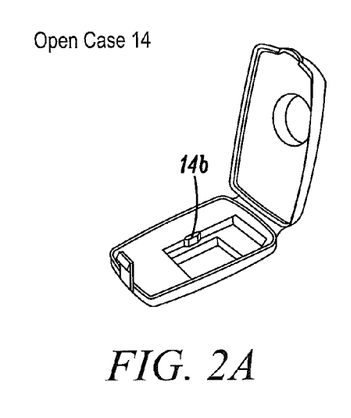
FIG. 2A-2E illustrate additional aspects of the system of FIG. 1.
Figure 2B:
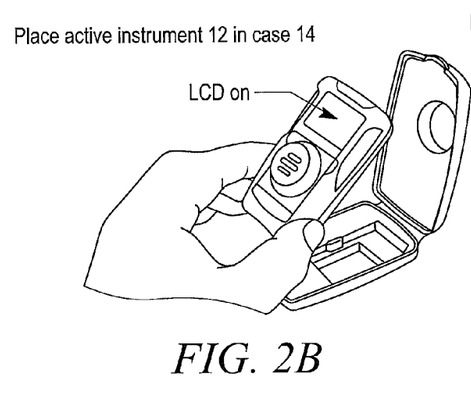
Figure 2C:
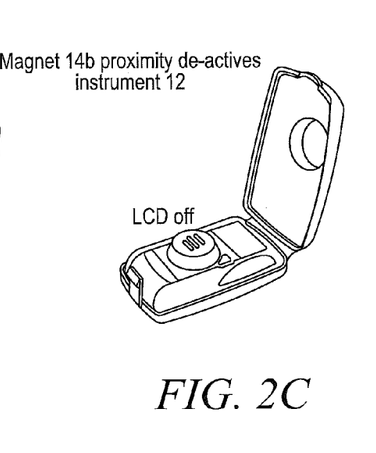
Figure 2D:
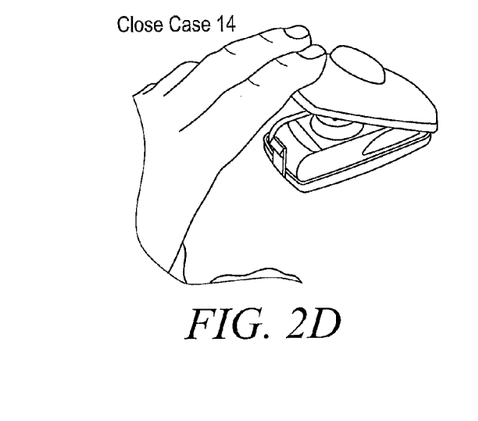
Figure 2E:
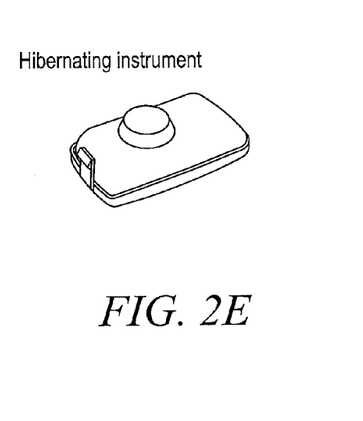

FIG. 2A illustrates an embodiment with a magnet functioning as the actuating device 14b. As illustrated in FIGS. 2A-2E, when detector 12 is inserted in case 14, the cover 14-1 can be closed completely isolating detector 12 in the sleep mode and providing immediate visual confirmation of the non-functionality of the detector 12.

Different types of gas detectors 12a, 12b can be used with case 14 so long as they exhibit the same form factor as defined by internal region 14a, and include appropriate sensors such as 26b.

Figure 3A:
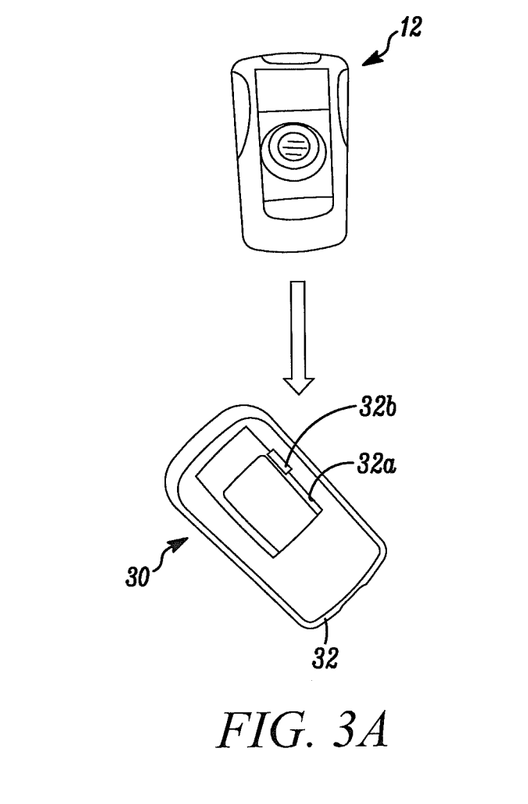
FIG. 3A illustrates a first state of a bump test.
Figure 3B:
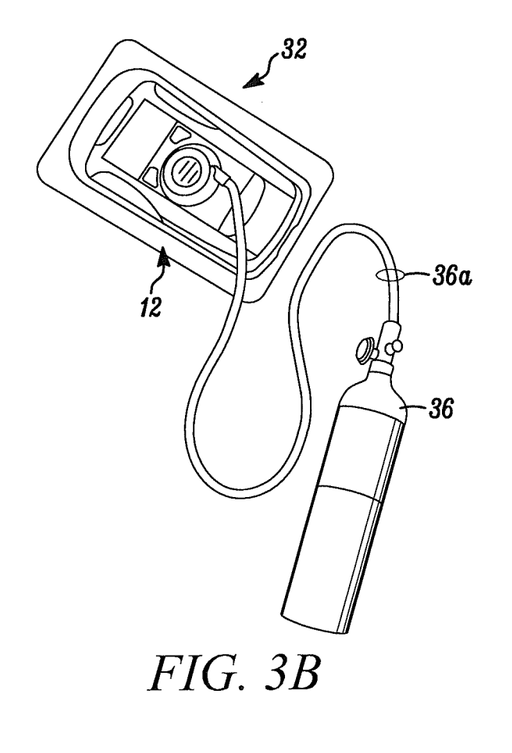
FIG. 3B illustrates a second state of a bump test.

FIGS. 3A, 3B illustrate another embodiment hereof. In FIG. 3A a bump test system 30 includes a cradle 32 with a receiving region 32a for a detector, such as detector 12, and an actuating element, for example, one or more bump magnets 32b.

When the detector 12 is inserted into the region 32a, it is brought into proximity of the magnetic field from the magnet(s) 32b. In a single magnet embodiment, a sensor, or, reader such as 26b in the detector 12 deciphers the orientation of the magnetic field. In this embodiment, bump test information is encoded by orientation of the magnetic field of magnet 32b.

In the case of a sensor 26b, with associated control circuits 28a, which are capable of deciphering the angle of a magnetic field accurate to one degree, it is possible to encode 360 states with a single magnet, such as 32b on the bump station 32. These states could represent different gasses, or in some cases, certain states could be reserved for future use.

Figure 4A:
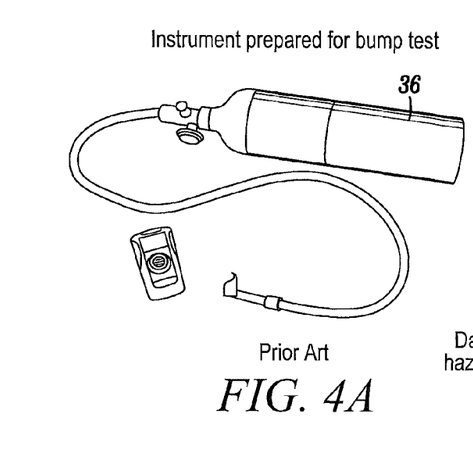
FIGS. 4A, B illustrate a prior art method of bump testing.
Figure 4B:
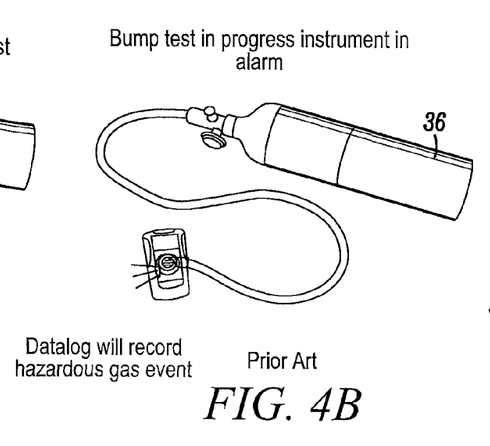

FIGS. 4A, 4B illustrate prior art bump testing. The detector being tested goes into alarm as it cannot distinguish a test from a hazardous event.

Figure 4C:
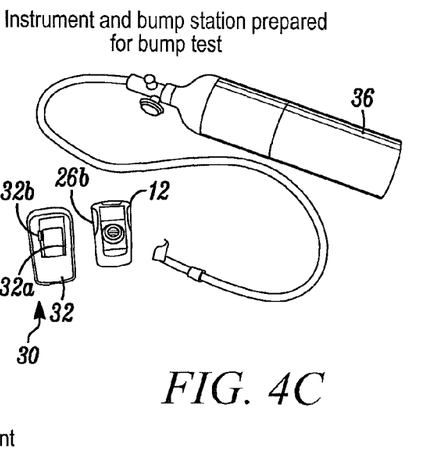
FIGS. 4C-4E illustrate bump testing in accordance herewith.
Figure 4D:
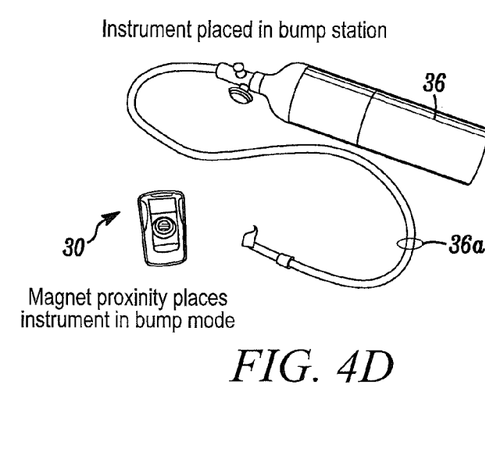
Figure 4E:
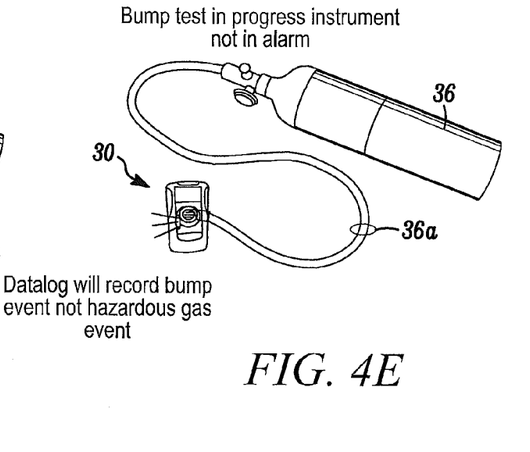
Figures 5A, 5B, 5C, 5D, 5E, 5F:
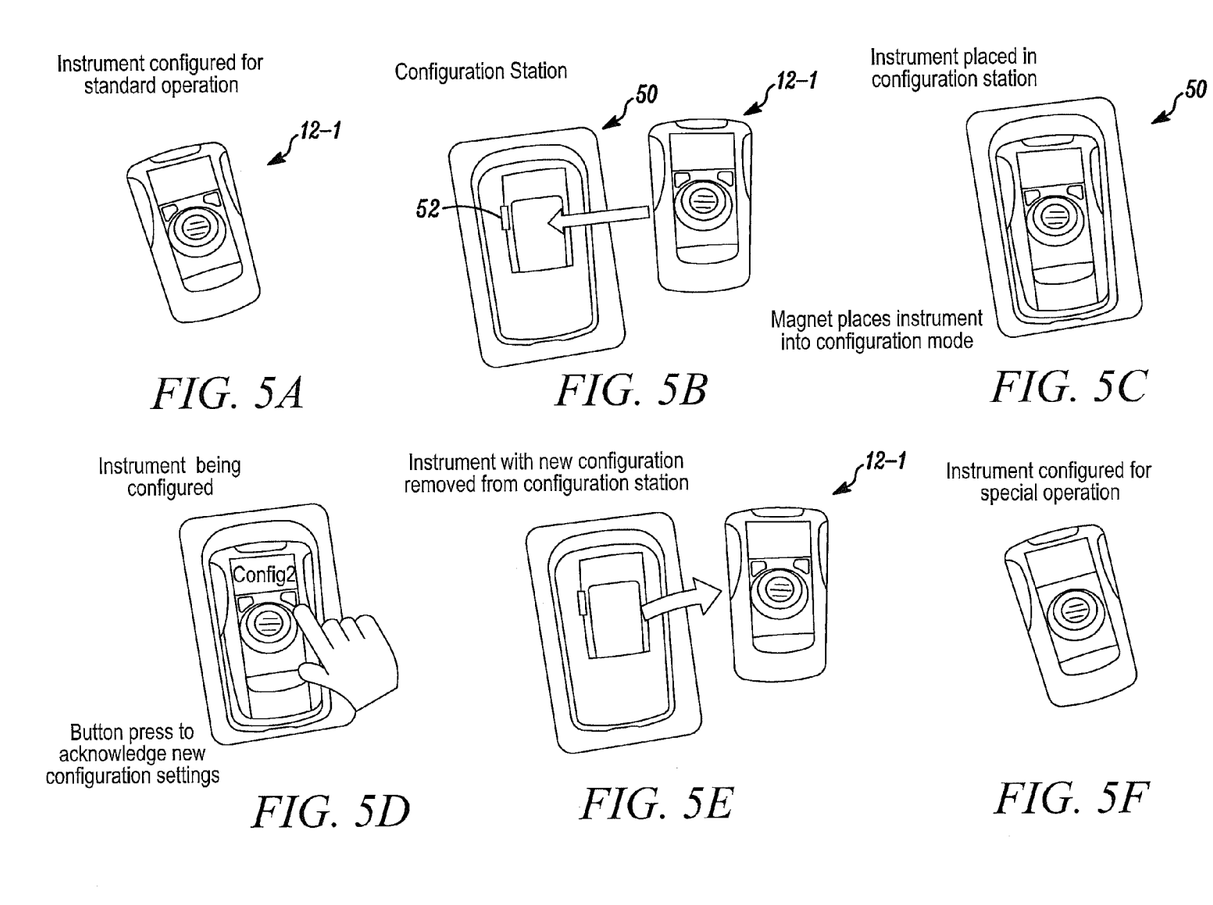
FIGS. 5A-5F illustrate a method of controlling and configuring a gas detector in accordance herewith.

With respect to FIGS. 4C-4E, when the detector 12 is inserted into the bump station cradle 32, and the orientation of the magnet 32b is decoded, an appropriate test gas from a container 36 can be coupled to the detector 12, via hose 36a. In this mode, the detector 12 recognizes that a bump test is being conducted and maintains an internal log of test activity without activating the audible alarm indicating device 22a. If the test is passed, the detector 12 can be returned to service. If not, a warning can be provided and detector 12 can be automatically shut down.

Those of skill in the art will understand that the system 30 of FIGS. 3A, 3B is not limited to magnetic actuators or sensors. Alternately, optical or RF communication come within the spirit and scope hereof.

FIGS. 5A-5F illustrate a process of configuring detectors, or other instruments in accordance herewith, using magnets and magnetic sensors. When a detector 12-1 is inserted into configuration station 50, it is brought into proximity of a magnetic field(s) from the magnet(s), such as magnet(s) 52. In a single magnet embodiment, a sensor, or, reader such as 26b in the detector 12-1 deciphers the orientation of the magnetic field. In this embodiment, control or test information is encoded by orientation of the magnetic field of magnet(s) 52. Multiple magnets can be used to provide a sequence of magnetic fields that could be detected by one or more sensors in the instrument 12-1.

In the case of a sensor, such as 26b, with associated control circuits 28a, which are capable of deciphering the angle of a magnetic field accurate to one degree, it is possible to encode 360 states with a single magnet, such as 52 on the station 50.

These states could represent for example, configurations such as, behavior or state alterations include changing alarm set points, changing bump test frequency, turning the device on or off, or altering sleep/operating modes of the detector.

Magnets, such as magnet(s) 52 can be used to meet the need of a low cost, low power, easy to use and safe way to configure the detector. Data can be transferred to the instrument 12-1 via a magnetic sensor in the instrument. When the detector 12-1 interfaces with a passive magnet array, it reads and deciphers control data. This data instructs the detector to implement any of a number of configuration changes, including but not limited to, entering a low power mode or state, exiting low power mode or state, changing alarm set points, or, preparing for bump test.

Removal of the detector 12-1 from the configuration station 50 places that instrument into the selected configuration until it is returned to the station 50.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. An apparatus comprising:
    a passive magnetic array; and
    a gas detector, wherein the gas detector comprises a gas sensor, and a magnetic sensor, wherein the magnetic sensor is configured to alter at least one configuration of the gas detector in response to detecting a control data transmission provided by the passive magnetic array;
    wherein the passive magnetic array comprises a magnet arranged at an angle with resect to the gas detector, and wherein the magnetic sensor is configured to detect an angular position of a magnetic field of the magnet, and wherein the angle of the magnetic field corresponds to the control data transmission.

2. The apparatus as in claim 1, wherein the configuration corresponds to at least one of an active/inactive state, a bump test indicator, or an operational parameter.

3. The apparatus as in claim 2, wherein the gas detector comprises circuitry to retain a remaining operational life time indicator, and wherein the remaining life time indicator is not altered when the detector is inactive.

4. The apparatus as in claim 2, wherein the configuration corresponds to a bump test indicator, and wherein in response to receiving the bump test indicator, the detector automatically stores bump test information.

5. The apparatus as in claim 2, wherein the configuration corresponds to a set point indicator, and wherein in response to the received set point indicator, a detector alarm set point is altered.

6. The apparatus as in claim 1, wherein the gas detector comprises circuitry to retain a remaining operation life time indicator, and wherein when the gas detector and the passive magnetic array are adjacent to one another, the gas detector becomes inactive with a fixed, remaining lifetime.

7. The apparatus as in claim 6, wherein the gas detector comprises a manual button to indicate that the gas detector is to become inoperable.

8. The apparatus as in claim 7, wherein the passive magnetic array is contained within a detector receiving enclosure, which receives the gas detector, at least in part.

9. The apparatus as in claim 8, wherein the manual button is carried on the gas detector, and wherein the gas detector is partly covered when the gas detector is in the detector receiving enclosure.

10. The apparatus as in claim 6, wherein the gas detector comprises circuitry that provides an indicator of remaining gas detector lifetime.

11. The apparatus as in claim 1, wherein the control data transmission comprises a bump test indicator, and, responsive thereto, the gas detector stores a record of the test.

12. The apparatus as in claim 1, wherein the control data transmission comprises an indicator of the type of gas used to perform the test.

13. An apparatus comprising:
a passive magnetic array; and
a gas detector, wherein the gas detector comprises a gas sensor, and a magnetic sensor, wherein the magnetic sensor is configured to alter at least one configuration of the gas detector in response to detecting a control data transmission provided by the passive magnetic array;
wherein the passive magnetic array comprises a series of magnets oriented in a North or South arrangement, wherein the magnetic sensor is configured to read magnetic orientations when the gas sensor is passed over the passive magnetic array, and wherein the magnetic orientations correspond to the control data transmission.

14. The apparatus as in claim 13, wherein the gas detector comprises circuitry to retain a remaining operational life time indicator, and wherein the remaining life time indicator is not altered when the detector is inactive.

15. The apparatus as in claim 13, wherein the gas detector comprises circuitry to retain a remaining operation life time indicator, and wherein when the gas detector and the passive magnetic array are adjacent to one another, the gas detector becomes inactive with a fixed, remaining lifetime.

16. The apparatus as in claim 15, wherein the gas detector comprises circuitry that provides an indicator of remaining gas detector lifetime.

17. An apparatus comprising:
a passive magnetic array; and
a gas detector, wherein the gas detector comprises a gas sensor, and a magnetic sensor, wherein the magnetic sensor is configured to alter at least one configuration of the gas detector in response to detecting a control data transmission provided by the passive magnetic array;
wherein the passive magnetic array comprises a linear array of magnets, wherein each magnet within the linear array of magnets comprises an angular orientation with respect to the gas sensor, wherein the magnetic sensor is configured to detect an angular position of each magnet within the linear array of magnets, and wherein the angular position of each magnet within the linear array of magnets corresponds to the control data transmission.

18. The apparatus as in claim 17, wherein the gas detector comprises circuitry to retain a remaining operational life time indicator, and wherein the remaining life time indicator is not altered when the detector is inactive.

19. The apparatus as in claim 17, wherein the gas detector comprises circuitry to retain a remaining operation life time indicator, and wherein when the gas detector and the passive magnetic array are adjacent to one another, the gas detector becomes inactive with a fixed, remaining lifetime.

20. The apparatus as in claim 19, wherein the gas detector comprises circuitry that provides an indicator of remaining gas detector lifetime.

* * * * *